United States Patent [19]

Davenport

[11] 4,283,403
[45] Aug. 11, 1981

[54] SUBSTITUTED ISOXAZOLINES FOR CONTROL OF PLANT PHYTOPATHOGENS

[75] Inventor: James D. Davenport, Indianapolis, Ind.

[73] Assignee: Eli Lilly and Company, Indianapolis, Ind.

[21] Appl. No.: 829,304

[22] Filed: Aug. 31, 1977

Related U.S. Application Data

[63] Continuation-in-part of Ser. No. 695,668, Jun. 14, 1976, abandoned.

[51] Int. Cl.$^3$ .................... C07D 413/04; A01N 43/80
[52] U.S. Cl. .................................... 424/263; 546/275
[58] Field of Search ................. 260/294.8 E; 424/263; 546/275

[56] References Cited

U.S. PATENT DOCUMENTS 3,471,523   10/1969   Harvey ................................. 260/349

OTHER PUBLICATIONS

Barroeta et al., Journal of the Chem. Soc., London, Perkin II, pp. 839–841 (1973).
Ettlinger et al., Journal of the American Chemical Society, vol. 77, pp. 1831–1836 (Apr. 1955).
Wagner–Juaregg, Chem. Abstracts, vol. 34, p. 6576, (Sep. 1940).

*Primary Examiner*—Alan L. Rotman
*Attorney, Agent, or Firm*—Kathleen R. S. Page; Arthur R. Whale

[57] ABSTRACT

A class of 2-isoxazolines bearing an aryl substituent at the 3-position and a substituted methyl or ethyl group at the 5-position effectively control microorganisms, particularly fungal foliar phytopathogens.

9 Claims, No Drawings

SUBSTITUTED ISOXAZOLINES FOR CONTROL OF PLANT PHYTOPATHOGENS

CROSS-REFERENCE TO RELATED APPLICATION

This application is a continuation-in-part of application Ser. No. 695,668, filed June 14, 1976, now abandoned.

BACKGROUND OF THE INVENTION

This invention belongs to the field of agricultural chemistry, and provides new compounds useful for the protection of plants from disease.

The control of harmful microorganisms has long been a major concern of chemical research. In particular, the control of phytopathogens was one of the first goals of agricultural chemistry, and research in the field continues at a high pitch.

SUMMARY OF THE INVENTION

The present invention provides new microbiocides of the formula

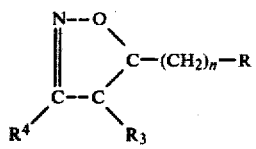

wherein
R represents
—NCS,
cyano,
amino,
amino hydrohalide,
—NHCSN ($R^1R^2$),
—NHCO$_2$($C_1$-$C_3$ alkyl) or

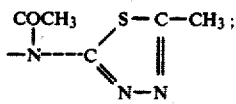

n represents 1 or 2;
$R^1$ and $R^2$ independently represent hydrogen or $C_1$-$C_3$ alkyl, or
$R^1$ represents hydrogen and $R^2$ represents amino, or
$R^1$ and $R^2$ combine with the nitrogen atom to which they are attached to form morpholino, piperidino or piperazino;
$R^3$ represents hydrogen or phenyl;
$R^4$ represents
naphthyl,
2-pyridyl or

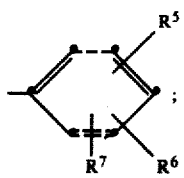

$R^5$, $R^6$ and $R^7$ independently represent
chloro,
bromo,
fluoro,
nitro,
trifluoromethyl,
$C_1$-$C_2$ alkoxy,
$C_1$-$C_2$ alkylthio,
$C_1$-$C_4$ alkyl,
hydroxy,
phenyl,
benzyloxy or
hydrogen,
provided that no more than one of $R^5$, $R^6$ and $R^7$ represents hydroxy, alkoxy, alkylthio, phenyl or benzyloxy; further provided that when one of $R^5$, $R^6$ and $R^7$ represents hydroxy, alkoxy, alkylthio or benzyloxy, (1) no more than one of $R^5$, $R^6$ and $R^7$ represents t-butyl;

(2) at least one of $R^5$, $R^6$ and $R^7$ represents chloro which is ortho or para to the hydroxy, alkoxy, alkylthio or benzyloxy group.

The new microbiocides provided herein are particularly useful against downy mildew of grape (*Plasmopara viticola*). As will be shown, various of such microbiocides also are effective against one or more of such fungal foliar phytopathogens as late blight of tomato (*Phytophthora infestans*), powdery mildew of bean (*Erysiphe polygoni*), rice blast (*Piricularia oryzae*), helminthosporium leaf spot of wheat (*Helminthosporium sativum*), botrytis of grape (*Botrytis cinerea*), apple scab (*Venturia inaequalis*), and cercospora leaf spot of sugar beet (*Cercospora beticola*).

The invention also provides a method of reducing the adverse effects of fungal foliar phytopathogens which comprises contacting the phytopathogens on the foliage of host plants with an effective amount of a compound described above. As already indicated, use on the foliage of grapes is particularly preferred. Fungicidal compositions containing the compounds are also provided.

DESCRIPTION OF THE PREFERRED EMBODIMENT

In the above formula, the terms $C_1$-$C_3$ alkyl, $C_1$-$C_4$ alkyl, $C_1$-$C_2$ alkoxy and $C_1$-$C_2$ alkylthio refer to groups such as methyl, ethyl, isopropyl, butyl, t-butyl, methoxy, ethoxy, methylthio and ethylthio. The term hydrohalide refers to hydrobromide, hydrochloride, hydrofluoride and hydroiodide.

The compounds of the formula above wherein R represents —NCS and $R^3$ represents hydrogen constitute a preferred class which have particularly good microbiocidal activity.

Throughout this document all temperatures are on the Celsius scale.

Further contemplated classes of compounds of the invention described above are those comprising the compounds wherein:

1. R represents —NCS;
2. R represents —NCS, cyano, NHCSN($R^1R^2$), or NHCO$_2$($C_1$-$C_3$ alkyl), wherein
   A. $R^1$ and $R^2$ represent hydrogen, $C_1$-$C_3$ alkyl or amino,
   B. $R^1$ and $R^2$ combine to form morpholino, piperidino or piperazino;
3. R represents NHCSN($R^1R^2$) or NHCO$_2$ ($C_1$-$C_3$ alkyl), wherein
   A. $R^1$ and $R^2$ represent hydrogen, $C_1$-$C_3$ alkyl or amino, B. $R^1$ and $R^2$ combine to form morpholino, piperidino or piperazino;

4. R represents cyano;

5. R represents —NCS, amino, amino hydrohalide, $NHCSN(R^1R^2)$ or $NHCO_2(C_1-C_3\,alkyl)$, wherein A. $R^1$ and $R^2$ represent hydrogen, $C_1-C_3$ alkyl or amino, B. $R^1$ and $R^2$ combine to form morpholino, piperidino or piperazino;

6. $R^3$ represents hydrogen;

7. $R^3$ represents phenyl;

8. $R^4$ represents 2-pyridyl;

9. $R^4$ represents naphthyl or

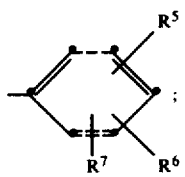

10. $R^4$ represents

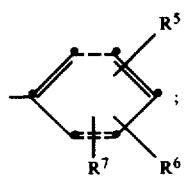

11. $R^3$ is as defined in subparagraph 6 above, and

A. R and $R^4$ are as defined in subparagraphs 1 and 8 above;

B. R and $R^4$ are as defined in subparagraphs 1 and 9 above;

C. R and $R^4$ are as defined in subparagraphs 1 and 10 above;

D. R and $R^4$ are as defined in subparagraphs 2A and 8 above;

E. R and $R^4$ are as defined in subparagraphs 2A and 9 above;

F. R and $R^4$ are as defined in subparagraphs 2A and 10 above;

G. R and $R^4$ are as defined in subparagraphs 2B and 8 above;

H. R and $R^4$ are as defined in subparagraphs 2B and 9 above;

I. R and $R^4$ are as defined in subparagraphs 2B and 10 above;

J. R and $R^4$ are as defined in subparagraphs 3 and 8 above;

K. R and $R^4$ are as defined in subparagraphs 3 and 9 above;

L. R and $R^4$ are as defined in subparagraphs 3 and 10 above;

M. R and $R^4$ are as defined in subparagraphs 4 and 8 above;

N. R and $R^4$ are as defined in subparagraphs 4 and 9 above;

O. R and $R^4$ are as defined in subparagraphs 4 and 10 above;

P. R and $R^4$ are as defined in subparagraphs 5A and 8 above;

Q. R and $R^4$ are as defined in subparagraphs 5A and 9 above;

R. R and $R^4$ are as defined in subparagraphs 5A and 10 above;

S. R and $R^4$ are as defined in subparagraphs 5B and 8 above;

T. R and $R^4$ are as defined in subparagraphs 5B and 9 above;

U. R and $R^4$ are as defined in subparagraphs 5B and 10 above.

12. $R^3$ is as defined in subparagraph 7 above, and

A. R and $R^4$ are as defined in subparagraphs 1 and 8 above;

B. R and $R^4$ are as defined in subparagraphs 1 and 9 above;

C. R and $R^4$ are as defined in subparagraphs 1 and 10 above;

D. R and $R^4$ are as defined in subparagraphs 2A and 8 above;

E. R and $R^4$ are as defined in subparagraphs 2A and 9 above;

F. R and $R^4$ are as defined in subparagraphs 2A and 10 above;

G. R and $R^4$ are as defined in subparagraphs 2B and 8 above;

H. R and $R^4$ are as defined in subparagraphs 2B and 9 above;

I. R and $R^4$ are as defined in subparagraphs 2B and 10 above;

J. R and $R^4$ are as defined in subparagraphs 3 and 8 above;

K. R and $R^4$ are as defined in subparagraphs 3 and 9 above;

L. R and $R^4$ are as defined in subparagraphs 3 and 10 above;

M. R and $R^4$ are as defined in subparagraphs 4 and 8 above;

N. R and $R^4$ are as defined in subparagraphs 4 and 9 above;

O. R and $R^4$ are as defined in subparagraphs 4 and 10 above;

P. R and $R^4$ are as defined in subparagraphs 5A and 8 above;

Q. R and $R^4$ are as defined in subparagraphs 5A and 9 above;

R. R and $R^4$ are as defined in subparagraphs 5A and 10 above;

S. R and $R^4$ are as defined in subparagraphs 5B and 8 above;

T. R and $R^4$ are as defined in subparagraphs 5B and 9 above;

U. R and $R^4$ are as defined in subparagraphs 5B and 10 above.

The compounds below are typical of the isoxazolines of this invention. It will be understood that the named compounds do not bound the scope of the invention, but are named merely to help agricultural chemists to understand the invention.

5-(2-cyanoethyl)-3-(1-naphthyl)-2-isoxazoline 5-aminomethyl-3-(2-naphthyl)-2-isoxazoline 5-(2-aminoethyl)-4-phenyl-3-(2-pyridyl)-2-isoxazoline, hydrobromide 5-(2-ethoxycarbonylaminoethyl)-3-(2,4,6-trichlorophenyl)-2-isoxazoline 3-(3-bromo-5-chlorophenyl)-5-propoxycarbonylaminomethyl-2-isoxazoline N-[[3-(2,4-difluorophenyl)-2-isoxazolin-5-yl]methyl]-N-(5-methyl-1,3,4-thiadiazol-2-yl)acetamide N-[2-[3-(2-hydroxy-5-nitrophenyl)-2-isoxazolin-5-yl]ethyl]-N-(5-methyl-1,3,4-thiadiazol-2-yl)acetamide 5-(2-isothiocyanatoethyl)-3-(2-trifluoromethylphenyl)-4-phenyl-2-isoxazoline 1-ethyl-3-[2-[3-(2,6-dinitro-4-trifluoromethylphenyl)-4-phenyl-2-isoxazolin-5-yl]ethyl]thiourea 1-propyl-3-[2-[3-(3-benzyloxy-5-methoxyphenyl)-2-isoxazolin-5-yl]ethyl]thiourea 1-ethyl-1-methyl-3-[2-[3-(3-chloro-2-ethoxyphenyl)-2-isoxazolin-5-yl]ethyl]thiourea 1,1-diethyl-3-[[3-(3,4-bis(methylthio)phenyl)-2-isoxazolin-5-yl]methyl]thiourea 1-isopropyl-1-methyl-3-[[3-(3-nitro-5-phenylphenyl)-2-isoxazolin-5-yl]methyl]thiourea 1-ethyl-3-[[3-(3-bromo-2,5-dihydroxyphenyl)-4-phenyl-2-isoxazolin-5-yl]methyl]thiourea N-[[3-(3-chloro-5-ethyl-4-hydroxyphenyl)-2-isoxazolin-5-yl]methyl]-4-morpholinethiocarboxamide N-[2-[3-(2,4-diisopropylphenyl)-2-isoxazolin-5-yl]ethyl]-1-piperidinethiocarboxamide N-[[3-(2,4,6-trimethylphenyl)-2-isoxazolin-5-yl]methyl]-1-piperazinethiocarboxamide 3-(4-benzyloxy-3-propylphenyl)-5-isothiocyanatomethyl-4-phenyl-2-isoxazoline 5-aminomethyl-3-[3-(t-butyl)-5-nitrophenyl]-2-isoxazoline, hydrofluoride 1-methyl-3-[2-[3-(2,5-diethylphenyl)-2-isoxazolin-5-yl]ethyl]thiourea 3-(2-chloro-6-nitrophenyl)-5-ethoxycarbonylaminomethyl-4-phenyl-2-isoxazoline 3-(3-chloro-5-nitrophenyl)-5-(2-isothiocyanatoethyl)-2-isoxazoline 1-[2-[3-(3,5-bis(trifluoromethyl)phenyl)-2-isoxazolin-5-yl]ethyl]thiourea 1-[[3-(2-hydroxy-4-trifluoromethylphenyl)-2-isoxazolin-5-yl]methyl]thiourea 5-aminomethyl-3-(2-chloro-5-ethylthio-3-phenylphenyl)-4-phenyl-2-isoxazoline 5-isothiocyanatomethyl-3-(3-methylthio-6-nitro-5-phenylphenyl)-2-isoxazoline The preferred compounds are 5-isothiocyanatomethyl-3-(4-chlorophenyl)-2-isoxazoline, 5-isothiocyanatomethyl-3-(4-trifluoromethylphenyl)-2-isoxazoline, 3-(2,6-dichlorophenyl)-5-isothiocyanatomethyl-2-isoxazoline, 5-isothiocyanatomethyl-3-(4-methylphenyl)-2-isoxazoline, and 5-isothiocyanatomethyl-3-(2-pyridyl)-2-isoxazoline.

The compounds of this invention are prepared by processes which are generally known in the organic chemical art, starting from readily obtainable starting compounds. The preparation of all of the compounds starts with an apropriately substituted arylaldehyde, a benzaldehyde when $R^4$ represents phenyl or substituted phenyl, a naphthaldehyde when $R^4$ represents naphthyl, or a pyridylaldehyde when $R^4$ represents 2-pyridyl.

In many cases, the starting aldehydes are available commercially from such firms as Aldrich Chemical Company, Inc., Milwaukee, WS, and Eastman Organic Chemicals, Eastman Kodak Company, Rochester, NY, among others.

In any event, all of the required starting aldehydes can be prepared readily by one having ordinary skill in the art utilizing well known procedures. For example, 38 preparative methods are summarized in Chapter 9 of R. B. Wagner and H. D. Zook, "Synthetic Organic Chemistry," John Wiley & Sons, Inc., New York, 1953, pp. 279–315.

In addition, various methods are discussed in such references as H. O. House, "Modern Synthetic Reactions," Second Ed., W. A. Benjamin, Inc., Menlo Park, CA, 1972. For example, at pp. 14–5 the Rosenmund reduction is discussed, which involves the hydrogenation of acyl chlorides in refluxing xylene in the presence of a palladium on barium sulfate catalyst (in the presence of a sulfur-quinoline poison). Lithium aluminum hydride reductions in diglyme or tetrahydrofuran, usually at −78° C., are discussed at pp. 72–3. The McFadyen-Stevens reduction of carboxylic acids is summarized at pp. 245–6. Finally, the oxidation of benzyl alcohols in methylene chloride at 25° C. with chromium trioxide in pyridine is discussed at p. 270.

Methods especially adapted to the preparation of pyridine-2-aldehyde also are well known in the art. For example, pyridine-2-aldehyde is obtained by the oxidation of 2-alkylpyridines with selenium dioxide, in the vapor phase at 400° C. in the presence of a catalyst comprising vanadium pentoxide with added oxides of molybdenum, chromium, or tin, or by heating with iodine in dimethylsulfoxide. See R. A. Abramovitch, Ed., "Pyridine and Its Derivatives," Supplement Part Two, Vol. 14 of The Chemistry of Heterocyclic Compounds, John Wiley & Sons, Inc., New York, 1974, pp. 308–11. Alternatively, ozonolysis of 2-vinylpyridine in methanol at −40° C. gives pyridine-2-aldehyde. Id., pp. 340–1. As a final example, the aldehyde also is obtained from the reaction of 2-pyridylmagnesium bromide with ethyl orthoformate. See Erwin Kingsberg, Ed., "Pyridine and Its Derivatives," Part Four, Vol. 14 of The Chemistry of Heterocyclic Compounds, Interscience Publishers, New York, 1964, p. 130.

The aldehyde is first reacted with hydroxylamine, preferably in the form of a hydrohalide salt, to form the corresponding aldehyde oxime. An acid scavenger, such as a tertiary amine, an alkali metal alkoxide, or an inorganic base such as sodium carbonate, sodium bicarbonate, potassium hydroxide and the like should be used when the hydroxylamine is used in the form of the hydrohalide. The preferred solvent is an aqueous alkanol, but other solvents, such as diethyl ether, chloroform and the like are also satisfactory. Reflux temperature is preferred.

The α-carbon of the aldehyde oxime is then chlorinated, as by simple contact with free chlorine in a solvent such as chloroform. Low temperatures from about 0° to about 10° are preferred.

The chlorination step also frequently chlorinates the phenyl ring of a benzaldoxime to some degree, particularly when a hydroxy, alkoxy, alkylthio or benzyloxy substituent is present. Thus, when such a substituent is present, the chlorination step usually gives a mixture of products with and without phenyl ring chlorination. In the absence of such a substituent, phenyl ring-chlorinated products normally are not isolated.

Since hydroxy, alkoxy, alkylthio and benzyloxy groups are ortho, para directing, phenyl ring chlorination occurs either ortho or para to such a group, with para being favored. Thus, one or more products are possible, depending upon the phenyl ring substitution pattern. For example, chlorination of 4-methoxybenzaldoxime gives only one product, α,3-dichloro-4-methoxybenzaldoxime, because of the symmetry of the 4-methoxyphenyl moiety. Chlorination of 3-methoxybenzaldoxime, on the other hand, can give three different products: α,2-dichloro-, α,4-dichloro-, and α,6-dichloro-3-methoxybenzaldoxime. Of course, the number of possible products can be diminished by the presence of other substituents. In fact, phenyl ring chlorination can be blocked completely if ortho and para positions are not available. However, labile groups, such as the t-butyl group, can in effect be displaced by chlorine if located ortho or para to a hydroxy, alkoxy, alkylthio or benzyloxy group. Thus, chlorination of 4-hydroxy-3,5-bis(t-butyl)benzaldoxime yields α,3-dichloro-4-hydroxy-5-(t-butyl)benzaldoxime.

While monochlorination of the phenyl ring is the most common, dichlorination can occur. The second chlorine, however, still most enter the ring ortho or para to a hydroxy, alkoxy, alkylthio or benzyloxy group. Because the first chlorine tends to deactivate the phenyl ring, the introduction of a second chlorine usually is not favored.

In view of the foregoing, it will be apparent to one having ordinary skill in the art that some poly-substituted α-chlorobenzaldoxime intermediates are most readily prepared by making use of such phenyl ring chlorination, as illustrated in the examples below.

The chlorinated oximes are the immediate precursors of all the compounds of this invention. They are unstable in the pure form and are used without purification.

The isothiocyanates, the preferred compounds of the invention, are prepared by contact of the chlorinated oxime at low temperature with allyl- or crotylisothiocyanate in the presence of a strong base, preferably triethylamine. When the desired product has a 4-phenyl substituent, the starting isothiocyanate is cinnamylisothiocyanate or 4-phenyl-3-butenylisothiocyanate. The preferred reaction solvent is diethyl ether, although other typical inert reaction solvents may be used, such as tetrahydrofuran, benzene, alkanes and the like. Triethylamine is the preferred strong base for reasons of convenience, but other typical strong bases, such as pyridine, sodium hydroxide, alkali metal alkoxides, lithium carbonate and the like may also be used effectively if desired.

The reaction temperature should be in the range of 0–15° C. although lower temperatures may be used. As usual in such reactions, the preferred sequence of addition is to combine the isothiocyanate and the oxime in the solvent, lower the temperature, and then add the base very slowly while stirring.

The same process is used to prepare the products where R represents cyano or alkylcarbamate by substituting an appropriate crytyl or allyl cyanide or carbamate for the isothiocyanate reactant.

The thioureas of this invention are prepared by simple reaction of the corresponding isothiocyanate with an appropriate amine. Reaction at temperatures from room temperature to reflux in reaction solvents such as diethyl ether or alkanols is satisfactory.

The products wherein R represents an amino group are prepared by hydrolyzing the corresponding carbamate, as with a strong mineral acid. The aminohydrohalides result when the mineral acid is a halogen acid, such as hydrochloric acid. The free amino compounds are prepared by neutralizing the hydrohalides with bases.

The methylthiadiazole products are prepared from the corresponding thioureas where $R^2$ represents amino by reaction with acetic anhydride, an acetyl halide or a mixture of both acetic anhydride and an acetyl halide. The preferred reaction conditions are reflux temperature in dioxane.

The following specific preparative examples are presented to assure that organic chemists can prepare any desired compound of the invention. The products of the following examples were identified by nuclear magnetic resonance analysis, elemental microanalysis, and in appropriate cases, infrared analysis and mass spectroscopy.

The first example illustrates a typical preparation of an isoxazolinyl isothiocyanate.

EXAMPLE 1

5-isothiocyanatomethyl-3-(4-chlorophenyl)-2-isoxazoline

One mole, 70 g., of hydroxylamine hydrochloride and 54 g. of sodium methoxide were added to 500 ml. of isopropanol and 250 ml. of water. A 130 g. portion of 4-chlorobenzaldehyde was added, and the reaction mixture was stirred overnight at room temperature. A large amount of water was then added, the resulting white precipitate was separated by filtration, and the filtrate was extracted with chloroform. The organic layer was dried over sodium sulfate and evaporated to one-half its volume. Three volumes of hexane was then added, and the product, 4-chlorobenzaldoxime, was recovered by filtration. The yield was 101 g.

The benzaldoxime was dissolved in one liter of chloroform and cooled to 5°–10°, and dry chlorine gas was bubbled through the solution. The resulting yellow solution was evaporated to dryness and was washed with hexane to produce 123 g. of α,4-dichlorobenzaldoxime.

A 20 g. portion of the above intermediate was dissolved in 750 ml. of anhydrous diethyl ether and 15 g. of allylisothiocyanate was added. The reaction mixture was cooled to 5°, and 15 g. of triethylamine in 125 ml. of anhydrous diethyl ether was added dropwise over 1 hour with stirring, while the temperature was held at 5°. The mixture was then stirred overnight and allowed to warm to room temperature. The reaction mixture was then filtered and the filtrate was evaporated under vacuum to a thick yellow oil which partially crystallized. The precipitate from the filtration was first washed with acetone, then with water, then with chloroform and finally extracted with chloroform: water. All of the chloroform portions were combined with the acetone wash and the residue from evaporation of the filtrate, and the mixture was concentrated under vacuum and diluted with hexane. Approximately 12 g. of 5-isothiocyanatomethyl-3-(4-chlorophenyl)-2-isoxazoline, m.p. 118°–120°, crystallized and was recovered by filtration.

The following example illustrates the preparation of an isothiocyanatoethyl compound, wherein n represents 2.

EXAMPLE 2

5-(2-isothiocyanatoethyl)-3-phenyl-2-isoxazoline

A 23 g. portion of α-chlorobenzaldoxime, prepared as in Example 1 above, was combined with 17 g. of crotylisothiocyanate in 300 ml. of diethyl ether. The solution was cooled to 15° and 40 ml. of triethylamine in 100 ml. of tetrahydrofuran was added dropwise. The mixture was stirred for 24 hours at 15°, and was then filtered. The filtrate was washed with water, and evaporated to dryness. The residue was dissolved in chloroform, and chromatographed over a column (2.5 cm. diameter by 8 meters long) of polystyrene gel beads. The eluate was evaporated to dryness, and the residue was recrystallized from diisopropyl etherhexane. The product was identified as 10 g. of 5-(2-isothiocyanatoethyl)-3-phenyl-2-isoxazoline, m.p. 54°–56°. The microanalytical results were as follows:

|   | Theoretical | Found |
|---|---|---|
| C | 62.04% | 61.77% |
| H | 5.21 | 5.02 |
| N | 12.06 | 11.93 |
| S | 13.80 | 14.03 |

The following isothiocyanates were all produced by processes essentially similar to those just described. Only the amounts of reactants and identifying characteristics of the following compounds will be indicated.

EXAMPLE 3

5-isothiocyanatomethyl-3-phenyl-2-isoxazoline

A 156 g. portion of α-chlorobenzaldoxime was reacted with 125 g. of allylisothiocyanate to produce 110 g. of product, m.p. 61°–63°.

|   | Theoretical | Found |
|---|---|---|
| C | 60.53% | 60.81% |
| H | 4.62 | 4.69 |
| N | 12.83 | 12.69 |
| S | 14.69 | 14.79 |

EXAMPLE 4

5-isothiocyanatomethyl-3-(2,4-dichlorophenyl)-2-isoxazoline

A 34 g. portion of 2,4-dichlorobenzaldoxime was chlorinated as in Example 1 and reacted with 20 g. of allylisothiocyanate to produce 6 g. of product, an oily liquid.

|   | Theoretical | Found |
|---|---|---|
| C | 46.01% | 46.24% |
| H | 2.81 | 2.72 |
| N | 9.76 | 9.85 |
| S | 11.17 | 11.06 |

EXAMPLE 5

5-isothiocyanatomethyl-3-(3-trifluoromethylphenyl)-2-isoxazoline

A chlorinated benzaldoxime was prepared from 18 g. of 3-trifluoromethylbenzaldehyde and was reacted with 15 g. of allylisothiocyanate to produce 7 g. of product, m.p. 47°–49°.

|   | Theoretical | Found |
|---|---|---|
| C | 50.35% | 50.23% |
| H | 3.17 | 3.13 |
| N | 9.79 | 9.74 |
| S | 11.20 | 11.05 |

EXAMPLE 6

3-(3-chloro-4-methoxy-5-methylphenyl)-5-isothiocyanatomethyl-2-isoxazoline

A 40 g. portion of α,3-dichloro-4-methoxy-5-methylbenzaldoxime was reacted with 25 g. of allylisothiocyanate to produce 100 mg. of product, m.p. 108°–108.5°.

|   | Theoretical | Found |
|---|---|---|
| C | 52.61% | 52.39% |
| H | 4.42 | 4.25 |
| N | 9.44 | 9.41 |
| Cl | 11.95 | 12.26 |

EXAMPLE 7

5-isothiocyanatomethyl-3-(2-naphthyl)-2-isoxazoline

A 21 g. portion of α-chloro-β-naphthaldoxime was reacted with 25 g. of allylisothiocyanate to produce 1 g. of product, an oily liquid, NMR multiplets at 3.28–4.15, 4.83–5.28 and 7.5–8.42 ppm.

EXAMPLE 8

3-(2-chlorophenyl)-5-isothiocyanatomethyl-2-isoxazoline

A 19 g. portion of α,2-dichlorobenzaldoxime was reacted with 15 g. of allylisothiocyanate to produce 9.5 g. of product, an oily liquid.

|   | Theoretical | Found |
|---|---|---|
| C | 52.28% | 52.56% |
| H | 3.59 | 3.37 |
| N | 11.08 | 10.85 |
| S | 12.69 | 12.97 |

EXAMPLE 9

3-(3-chlorophenyl)-5-isothiocyanatomethyl-2-isoxazoline

A 40 g. portion of α,3-dichlorobenzaldoxime was reacted with 10 g. of allylisothiocyanate to produce 6 g. of product, an oily liquid.

|   | Theoretical | Found |
|---|---|---|
| C | 52.28% | 52.43% |
| H | 3.59 | 3.72 |
| N | 11.08 | 10.87 |
| Cl | 14.02 | 14.98 |
| S | 12.69 | 12.58 |

EXAMPLE 10

5-isothiocyanatomethyl-3-(4-nitrophenyl)-2-isoxazoline

A 12.5 g. portion of 4-nitrobenzaldehyde was converted to the chlorinated oxime, and reacted with 15 g. of allylisothiocyanate to produce 1 g. of product, m.p. 136°–138°.

|   | Theoretical | Found |
|---|---|---|
| C | 50.18% | 50.47% |
| H | 3.45 | 3.52 |
| N | 15.96 | 15.69 |
| S | 12.18 | 11.98 |

EXAMPLE 11

5-isothiocyanatomethyl-3-(4-trifluoromethylphenyl)-2-isoxazoline

A 175 g. portion of 4-trifluoromethylbenzaldehyde was converted to the chlorinated oxime, and reacted with 200 g. of allylisothiocyanate to produce 199 g. of product, m.p. 124°–126°.

|   | Theoretical | Found |
|---|---|---|
| C | 50.35% | 50.55% |
| H | 3.17 | 3.27 |
| N | 9.79 | 9.54 |
| S | 11.20 | 11.23 |

EXAMPLE 12

3-(2,6-dichlorophenyl)-5-isothiocyanatomethyl-2-isoxazoline

A 35 g. portion of 2,6-dichlorobenzaldoxime was chlorinated on the α-carbon, and reacted with 25 g. of allylisothiocyanate to produce 7 g. of product, m.p. 64°–66°.

|   | Theoretical | Found |
|---|---|---|
| C | 46.01% | 45.82% |
| H | 2.81 | 2.80 |
| N | 9.76 | 9.97 |
| S | 11.17 | 11.01 |

EXAMPLE 13

3-(3-chloro-4-methoxyphenyl)-5-isothiocyanatomethyl-2-isoxazoline

EXAMPLE 14

5-isothiocyanatomethyl-3-(4-methoxyphenyl)-2-isoxazoline

A 28 g. portion of 4-methoxybenzaldoxime was chlorinated, and reacted with 25 g. of allylisothiocyanate as in Example 1. Chromatography of the product mixture isolated 9 g. of 3-(3-chloro-4-methoxyphenyl)-5-isothiocyanatomethyl-2-isoxazoline, m.p. 92°–94° and 90 mg. of 5-isothiocyanatomethyl-3-(4-methoxyphenyl)-2-isoxazoline, an oily liquid.

| (Example 13) |   | Theoretical | Found |
|---|---|---|---|
|   | C | 50.98% | 51.25% |
|   | H | 3.92 | 4.00 |
|   | N | 9.91 | 9.67 |
|   | S | 11.34 | 11.33 |
| (Example 14) |   | Theoretical | Found |
|   | C | 46.01% | 46.24% |
|   | H | 2.81 | 2.72 |
|   | N | 9.76 | 9.85 |
|   | S | 11.17 | 11.06 |

EXAMPLE 15

5-isothiocyanatomethyl-3-(4-methylphenyl)-2-isoxazoline

A 29 g. portion of 4-methylbenzaldoxime was chlorinated and reacted with 25 g. of allylisothiocyanate to produce 4.1 g. of product, m.p. 80.5°–81°.

|   | Theoretical | Found |
|---|---|---|
| C | 62.04% | 61.76% |
| H | 5.21 | 5.18 |
| N | 12.06 | 11.96 |
| S | 13.80 | 14.05 |

EXAMPLE 16

3-(4-bromophenyl)-5-isothiocyanatomethyl-2-isoxazoline

A 10 g. portion of 4-bromobenzaldoxime was chlorinated and reacted with 10 g. of allylisothiocyanate to prepare 15 g. of product, m.p. 123°–125°.

|   | Theoretical | Found |
|---|---|---|
| C | 44.46% | 44.21% |
| H | 3.05 | 3.15 |
| N | 9.43 | 9.20 |
| S | 10.79 | 10.80 |

EXAMPLE 17

3-(4-fluorophenyl)-5-isothiocyanatomethyl-2-isoxazoline

A 12.5 g. portion of 4-fluorobenzaldoxime was chlorinated and reacted with 50 ml. of allylisothiocyanate to prepare 3.4 g. of product, m.p. 59°–61°.

|   | Theoretical | Found |
|---|---|---|
| C | 55.92% | 56.08% |
| H | 3.84 | 3.95 |
| N | 11.86 | 12.25 |
| S | 13.59 | 13.92 |

EXAMPLE 18

3-(2-isopropylphenyl)-5-isothiocyanatomethyl-2-isoxazoline

One g. of 2-isopropylbenzaldehyde was converted to the oxime and chlorinated, and then reacted with 20 g. of allylisothiocyanate to produce 100 mg. of product, an oily liquid.

|   | Theoretical | Found |
|---|---|---|
| C | 64.59% | 64.36% |
| H | 6.19 | 5.92 |
| N | 10.76 | 10.43 |
| S | 12.32 | 12.62 |

EXAMPLE 19

3-(4-isopropylphenyl)-5-isothiocyanatomethyl-2-isoxazoline

Fifteen g. of 4-isopropylbenzaldehyde was converted to the oxime, chlorinated and reacted with 20 g. of allylisothiocyanate to produce 2 g. of product, m.p. 68°–70°.

|   | Theoretical | Found |
|---|---|---|
| C | 64.59% | 64.31% |
| H | 6.19 | 6.00 |
| N | 10.76 | 10.45 |
| S | 12.32 | 12.38 |

EXAMPLE 20

5-isothiocyanatomethyl-3-(2-pyridyl)-2-isoxazoline

Twelve g. of 2-pyridinaldoxime was chlorinated and reacted with 25 ml. of allylisothiocyanate to produce 14 g. of product, a liquid.

|   | Theoretical | Found |
|---|---|---|
| C | 54.78% | 54.70% |
| H | 4.14 | 4.09 |
| N | 19.16 | 18.94 |

EXAMPLE 21

5-isothiocyanatomethyl-3-(4-phenylphenyl)-2-isoxazoline

A 17 g. portion of 4-phenylbenzaldehyde was converted to the oxime, chlorinated and reacted with 25 ml. of allylisothiocyanate to produce 6 g. of product, m.p. 162°–164° C.

|   | Theoretical | Found |
|---|---|---|
| C | 69.36% | 69.65% |
| H | 4.79 | 4.75 |
| N | 9.52 | 9.39 |
| S | 10.89 | 11.11 |

EXAMPLE 22

3-[3-chloro-4-hydroxy-5-(t-butyl)phenyl]-5-isothiocyanatomethyl-2-isoxazoline

A 25 g. portion of 4-hydroxy-3,5-bis(t-butyl)benzaldoxime was chlorinated as in Example 1 to produce 1 g. of α,3-dichloro-4-hydroxy-5-(t-butyl)benzaldoxime by chlorination and rearrangement. The intermediate was reacted with an excess of allylisothiocyanate to produce 1 g. of product, an oily liquid, NMR singlets at 1.41 and 6.18 ppm., multiplets at 2.92–3.93, 4.68–5.23 and 7.5–7.63 ppm.

EXAMPLE 23

5-isocyanatomethyl-3,4-diphenyl-2-isoxazoline

A 3.5 g. portion of cinnamylisothiocyanate was reacted with 5 g. of α-chlorobenzaldoxime as in Example 1 to produce 1 g. of the product, m.p. 94°–96° C., NMR multiplets at 3.62–4.12, 5.65–5.78 and 7.22–7.83 ppm.

EXAMPLE 24

3-(3-chloro-4-benzyloxyphenyl)-5-isothiocyanatomethyl-2-isoxazoline

EXAMPLE 25

3-(3,5-dichloro-4-benzyloxyphenyl)-5-isothiocyanatomethyl-2-isoxazoline

A 21 g. portion of 4-benzyloxybenzaldehyde was converted to the oxime, and chlorinated. Two chlorinated products were obtained, α,3-dichloro-4-benzyloxybenzaldoxime and α,3,5-trichloro-4-benzyloxybenzaldoxime. The reaction of the intermediate mixture with 20 g. of allylisothiocyanate produced 5.4 g. of 3-(3-chloro-4-benzyloxyphenyl)-5-isothiocyanatomethyl-2-isoxazoline and 1.38 g. of 3-(3,5-dichloro-4-benzyloxyphenyl)-5-isothiocyanatomethyl-2-isoxazoline, both oily liquids, showing the following NMR features.

| Example 24 | Example 25 |
|---|---|
| 2.83–3.82 ppm. | 2.77–3.83 ppm. |
| 4.63–5.20 | 4.60–5.28 |
| 5.17 | 5.05 |
| 6.96 | 7.20–7.78 |
| 7.25–7.78 | |

The following example illustrates the synthesis of compounds of this invention having a nitrile substituent.

EXAMPLE 26

5-cyanomethyl-3-phenyl-2-isoxazoline

A 60 g. portion of benzaldoxime was chlorinated in chloroform at 10° C. with dry gaseous chlorine, and the reaction mixture was evaporated to dryness. The residue was taken up in tetrahydrofuran:ether and combined with 100 g. of allyl cyanide. The reaction mixture was cooled to 10° C., and 100 g. of triethylamine was added dropwise, keeping the temperature below 20° C. at all times. The mixture was stirred overnight. A large amount of water was added, and the organic layer was separated. The water layer was extracted with diethyl ether and the ether layer was combined with the organic layer from the reaction mixture. The combined organics were evaporated to a thick oil which was crystallized from chloroform to yield 62 g. of 5-cyanomethyl-3-phenyl-2-isoxazoline, m.p. 79°–80.5° C.

|   | Theoretical | Found |
|---|---|---|
| C | 70.95% | 70.56% |
| H | 5.41 | 5.55 |
| N | 15.04 | 14.77 |

The following examples illustrate the synthesis of typical thiourea compounds of this invention.

EXAMPLE 27

4-[[3-(4-chlorophenyl)-2-isoxazolin-5-yl]methyl]-3-thiosemicarbazide

A 25 g. portion of the product of Example 1 was reacted with excess hydrazine in 200 ml. of ethanol for 2 hours, allowing the reaction to heat to reflux temperature. The solids which precipitated upon cooling were separated by filtration and identified as 27 g. of product, m.p. 115°–117°, NMR singlets at 4.48, 7.4, 7.63, 7.97 and 8.73 ppm., and multiplets at 3.05–4.12 and 4.67–5.28 ppm.

EXAMPLE 28

1,1-diisopropyl-3-[[3-(4-methylphenyl-2-isoxazolin-5-yl]-methyl]thiourea

Five g. of the product of Example 15 was reacted with excess diisopropylamine neat at room temperature for 7 days. The reaction mixture was chromatographed over a 12-meter silica gel column with methyl ethyl ketone as the eluting solvent. The desired product was in the first fraction off the column. The solvents were evaporated and the product obtained was 1 g. of 1,1-diisopropyl-3-[[3-(4-methylphenyl-2-isoxazolin-5-yl]methyl]thiourea, an oily liquid, NMR singlets at 2.37, 5.82, 7.15 and 7.52 ppm., and multiplets at 1.15–1.37, 2.87–3.72, 3.98–4.2 and 4.37–5.25 ppm.

EXAMPLE 29

N-[[3-(3-trifluoromethylphenyl)-2-isoxazolin-5-yl]methyl]-4-morpholinethiocarboxamide One hundred mg. of the product of Example 5 was reacted with excess morpholine to produce 100 mg. of product, m.p. 118°–120°.

|   | Theoretical | Found |
|---|---|---|
| C | 51.47% | 51.54% |
| H | 4.83 | 4.44 |
| N | 11.26 | 11.03 |
| S | 8.58 | 8.41 |

EXAMPLE 30

N-[2-(3-phenyl-2-isoxazolin-5-yl)ethyl]-4-morpholinethiocarboxamide

One hundred mg. of the product of Example 2 was reacted with excess morpholine to produce 100 mg. of product, m.p. 128°–130° C.

|   | Theoretical | Found |
|---|---|---|
| C | 60.19% | 60.19% |
| H | 6.58 | 5.30 |
| N | 13.17 | 12.97 |
| O | 10.03 | 11.09 |
| S | 10.03 | 10.07 |

EXAMPLE 31

1-[[3-(4-chlorophenyl)-2-isoxazolin-5-yl]methyl]-3-methylthiourea

To 3 g. of the product of Example 1 was added 5 ml. of 40 percent methylamine in aqueous ethanol. The mixture was stirred for 1 hour, and was then allowed to stand overnight. The product separated as a precipitate, which was collected and recrystallized from methanol-water, and recrystallized a second time from chloroform to produce 0.8 g. of product, m.p. 131°–133° C.

|   | Theoretical | Found |
|---|---|---|
| C | 50.79% | 50.92% |
| H | 4.97 | 4.86 |
| N | 14.81 | 14.68 |
| Cl | 12.49 | 12.74 |
| S | 11.30 | 11.29 |

EXAMPLE 32

5-methoxycarbonylaminomethyl-3-phenyl-2-isoxazoline

A 24 g. portion of benzaldoxime was chlorinated, isolated and dissolved in diethyl ether. The solution was cooled to 15° C., and 46 g. of methyl allylcarbamate was added. Sixty ml. of triethylamine was then added dropwise, keeping the temperature below 20° C. The mixture was stirred for 3 hours, and filtered. The filtrate was evaporated to dryness, and the residue was washed with water and filtered again. The solids were identified as 32 g. of product, m.p. 102°–103° C., NMR singlets at 3.63 and 5.48 ppm., multiplets at 2.82–3.80, 4.57–5.08, 7.13–7.50 and 7.45–7.77 ppm.

The following example illustrates the preparation of amino compounds of the present invention.

EXAMPLE 33

5-aminomethyl-3-phenyl-2-isoxazoline

A 5 g. portion of the product of Example 32 was slurried in 50 percent aqueous hydrochloric acid and refluxed overnight. The mixture was then cooled and neutralized with potassium hydroxide, and extracted with chloroform. The chloroform layer was concentrated to 10 ml., and eluted through a 12-meter column of polystyrene gel beads with chloroform as the eluting solvent. The desired product was the second fraction off the column. The yield was 2 g. of 5-aminomethyl-3-phenyl-2-isoxazoline, an oily liquid, NMR multiplets at 2.57–3.83, 4.43–4.97, 7.08–7.60 and 7.42–7.80 ppm., and a singlet at 1.38 ppm.

The next example illustrates the preparation of the thiadiazoles of the present invention.

EXAMPLE 34

N-[[3-(4-chlorophenyl)-2-isoxazolin-5-yl]methyl]-N-(5-methyl-1,3,4-thiadiazol-2-yl)acetamide A 5 g. portion of the product of Example 27 was treated with 100 ml. of acetic anhydride and 50 ml. of acetyl chloride at reflux temperature in 100 ml. of dioxane until the mixture became clear. The reaction mixture was then evaporated under vacuum to a thick slurry. Fifty ml. of chloroform was added, and the mixture was filtered. The filtrate was evaporated to dryness and dissolved in 25 ml. of concentrated sulfuric acid, and stirred overnight at room temperature. The acid suspension was then poured into water, and the aqueous suspension was filtered to produce 5 g. of N-[[3-(4-chlorophenyl)-2-isoxazolin-5-yl]methyl]-N-(5-methyl-1,3,4-thiadiazol-2-yl)acetamide, m.p. 195°–197°, NMR singlets at 2.43, 2.63, 7.55 and 7.78 ppm., and multiplets at 3.00–3.92, 4.23–4.53 and 4.88–5.50 ppm.

The compounds of this invention have been tested to evaluate their ability to protect plants from the adverse effects of fungal foliar phytopathogens. The following examples illustrate the tests employed and the results produced by representative compounds.

In most of the tests, each compound was formulated for testing by dissolving or suspending about 3.5 weight percent of it in 50:50 acetone:ethanol containing about 10 g./100 ml. of a nonionic surfactant. The solution was then dispersed in deionized water in a quantity such that the water dispersion contained the various compound concentrations indicated in the specific test methods and the table below. Concentrations are measured in parts per million, by weight (ppm.).

In most of the tests, the compound dispersions were applied to the test plants by spraying them with an air atomizer, using sufficient dispersion to wet the plants thoroughly. Other methods of formulation and application were used in a few tests, as described in the specific test methods which follow.

Untreated, infected controls and untreated, normal controls were included in each test. The results are reported on a 1–5 rating scale where 1 indicates severe disease and 5 indicates complete control of the disease. An empty space in the table below shows that the indicated compound was not tested at the indicated rate. In some cases, more than one test was performed against a given phytopathogen, and the results in such cases are reported as averages. Compounds are identified by the example numbers used above.

Test 1 late blight of tomato

Four-week-old tomato seedlings were sprayed with aqueous dispersions containing test compounds at compound concentrations indicated in the table below. The following day, the foliage was inoculated with an aqueous suspension of propagules of *Phytophthora infestans*. The inoculum had been reared on infected wheat seed. The plants were held for two days in a moist chamber, and were then transferred to the greenhouse. The plants were observed and rated for disease control about one week after application of the test compounds.

Test 2 powdery mildew of bean

The host plants were 10-day-old bean seedlings. After aqueous dispersions containing test compounds at compound concentrations indicated in the table below had been sprayed on the foliage of the beans and allowed to dry, the plants were placed in the greenhouse and inoculated by storing them under other bean plants which were heavily infected with powdery mildew (*Erysiphe polygoni*). After about 10 days, the plants were observed and the results recorded as usual.

Test 3 anthracnose of cucumber

Aqueous dispersions containing test compounds at compound concentrations indicated in the table below were applied to healthy cucumber seedlings grown in sterilized greenhouse soil. The following day, the plants were inoculated with *Colletotrichum lagenarium* conidia as an aqueous suspension. The fungus had been grown on potato dextrose agar in petri dishes. The plants were held in a moist chamber for two days and transferred to the greenhouse, and the disease was observed and rated approximately 12 days after application of the test compounds.

Test 4 rice blast of rice

The test compound dispersions, at compound concentrations indicated in the table below, were applied to healthy rice seedlings growing thickly in plastic pots. The plants were inoculated on the next day with *Piricularia oryzae* (grown on rice polish agar) and the plants were held in a moist chamber for two days. The plants were then held in the greenhouse for 5-7 days and observed.

Test 5 helminthosporium leaf spot of wheat

Healthy wheat seed was planted in sterile greenhouse soil. When the seedlings were 4-5 inches tall, they were sprayed with test compound dispersions at compound concentrations indicated in the table below. The day after treatment, the plants were inoculated with a spore suspension of *Helminthosporium sativum* which had been grown on potato dextrose agar. The plants were placed in a moist growth chamber for two days to start disease growth, and were then transferred to the greenhouse. About a week after treatment, the plants were observed and the results were recorded.

Test 6 botrytis of grape

Sound grape berries were sterilized by immersion in diluted sodium hypochlorite and thoroughly rinsed. The berries were placed on wire screen shelves in compartmented Pyrex plates. The berries were then flamed and sprayed with test chemical dispersions. The following day, the berries were inoculated by spraying 5 ml. of a conidial suspension of *Botrytis cinerea* over each plate containing 12 berries. The inoculum had been grown in frozen lima bean agar. A small amount of water was added to each plate and a cover was sealed over each plate. After 48 hours at 25° C., the berries were observed and disease ratings recorded.

Test 7 apple scab of apple

Apple seedlings at the 4-6 leaf stage were sprayed with aqueous dispersions of the test compounds. The following day, the plants were sprayed with a suspension of fresh conidia of *Venturia inaequalis* obtained from infected apple seedlings kept as a source of inoculum. The plants were held for two days in a 20° moist chamber to start disease growth and were then transferred to the greenhouse. About two weeks after application of the compounds, the plants were observed and the results were recorded.

Test 8 downy mildew of grape

Young expanding grape leaves were detached from healthy vines on the day of the test. Leaves were placed individually in plastic petri dishes, bottom side up, on top of an expanded plastic mat. Water was added to each petri dish, and the petiole of each leaf was wrapped with a water-soaked wad of cotton. Each leaf was sprayed with an aqueous dispersion of the compound to be tested.

After the test compound dispersions had dried, the leaves were inoculated by atomizing a conidial suspension of *Plasmopara viticola* (grown on infected leaf tissue) evenly over the leaf surface. The plates were then covered and were stored in a growth room at about 18° and 100% relative humidity where they were exposed to 8 hours a day of artificial light. After about a week of storage, all the leaves were observed and the signs of disease were evaluated.

Test 9 cercospora leaf spot of sugar beet

Sugar beet seedlings were transplanted into square plastic pots and allowed to grow for three weeks. Aqueous dispersions containing 400 ppm. of the compounds to be tested were sprayed on the leaf surfaces. After the dispersions dried, but within 24 hours, the plants were inoculated with a conidial suspension of *Cercospora beticola* which had been grown on sugar beet leaf decoction agar. After the plants were held in a moist chamber for two days, they were transferred to the greenhouse and observed 2-3 weeks later.

| Compound of Example No. | Appln. Rate ppm. | Late Blight | Powdery Mildew | Anthracnose | Rice Blast | Helminthosporium | Botrytis | Apple Scab | Downy Mildew | Cercospora |
|---|---|---|---|---|---|---|---|---|---|---|
| 1 | 400 | 4 | 1 | 2 | 1 | 1 | 1 | | | |
|   | 80  | 4 |   | 1 |   |   |   | | | |
|   | 16  | 2 |   | 1 |   |   |   | | | |
|   | 3.2 | 1 |   |   |   |   |   | | | |
| 2 | 400 |   | 1 | 1 | 2 |   | 1 |   | 4 | 4 |
|   | 100 |   |   |   |   |   |   |   | 4 | 4 |
|   | 25  |   |   |   |   |   |   |   | 1 | 4 |
| 3 | 400 |   | 1 | 1 | 1 |   | 1 |   |   |   |
| 4 | 400 | 1 | 1 | 1 | 1 | 1 | 1 | 4 | 1 | 1 |
| 5 | 400 | 1 | 4 | 1 | 2 | 1 | 1 | 5 |   | 1 |
|   | 100 |   |   |   | 1 |   |   |   | 5 |   |
|   | 25  |   |   |   | 1 |   |   |   | 4 |   |
| 6 | 400 | 1 | 1 | 2 | 1 | 2 | 1 | 1 | 4 | 1 |
|   | 100 |   |   |   |   | 1 |   |   | 4 |   |
|   | 25  |   |   |   |   |   |   |   | 3 |   |
|   | 6   |   |   |   |   |   |   |   | 3 |   |
| 7 | 400 | 1 | 1 | 1 | 3 | 1 | 1 | 2 |   | 1 |
|   | 100 |   |   |   | 1 |   |   | 1 |   |   |
|   | 25  |   |   |   | 1 |   |   | 1 |   |   |
| 8 | 400 |   | 1 | 1 | 3 |   | 1 |   |   |   |
| 9 | 400 | 1 | 2 | 1 | 1 | 1 | 1 |   | 4 | 1 |
| 10 | 400 | 1 | 1 | 1 | 4 | 3 | 4 | 1 |   | 4 |
|    | 100 |   |   |   | 3 |   |   |   |   | 4 |
|    | 25  |   |   |   | 1 |   |   |   |   | 1 |
| 11 | 400 | 1 | 1 | 1 | 2 | 4 | 4 | 4 | 5 | 4 |
|    | 100 |   |   |   |   | 4 |   |   | 5 | 3 |
|    | 25  |   |   |   |   | 3 |   |   | 5 | 1 |
| 12 | 400 | 1 | 1 | 1 | 4 | 1 | 1 | 3 | 5 | 1 |
|    | 100 |   |   |   | 3 |   |   |   | 4 |   |
|    | 25  |   |   |   | 1 |   |   |   | 1 |   |
| 13 | 400 | 1 | 1 | 1 | 1 | 3 | 1 | 1 | 5 | 2 |
|    | 100 |   |   |   |   |   |   |   | 1 | 1 |
|    | 25  |   |   |   |   |   |   |   | 1 | 1 |
| 14 | 400 |   | 1 | 1 | 1 |   | 1 |   |   |   |
| 15 | 400 | 1 | 1 | 3 | 3 | 3 | 1 | 3 | 5 | 2 |
|    | 100 |   |   | 1 | 3 | 1 |   |   | 1 | 1 |
|    | 25  |   |   | 1 | 1 | 1 |   |   | 1 | 1 |
| 16 | 400 |   | 1 | 1 | 1 | 3 | 1 |   | 5 | 1 |
| 17 | 400 | 1 | 1 | 1 | 2 | 1 | 4 |   | 4 | 1 |
| 18 | 400 | 1 | 1 | 1 | 1 | 1 | 1 |   | 5 | 1 |
| 19 | 400 |   | 3 | 1 | 4 | 1 | 1 |   |   |   |
| 20 | 400 | 1 | 1 | 1 | 1 | 1 |   | 5 | 4 | 1 |
| 21 | 400 | 1 | 1 | 2 | 1 | 1 | 1 | 1 | 1 | 1 |
| 22 | 400 | 1 | 1 | 1 | 1 |   |   |   | 5 | 1 |
| 23 | 400 | 1 | 1 | 1 | 1 |   |   |   | 5 | 5 |
| 24 | 400 | 1 | 1 | 1 | 1 |   |   |   | 4 | 4 |
| 25 | 400 | 1 | 1 | 1 | 1 |   |   |   | 4 | 4 |
| 26 | 400 | 1 | 1 | 1 | 1 | 1 | 1 | 1 |   | 1 |
| 27 | 400 | 1 | 1 | 1 | 1 | 1 | 1 | 1 | 1 | 1 |
| 28 | 400 | 1 | 1 | 1 | 1 | 1 | 1 | 1 |   | 1 |
| 29 | 400 | 1 | 1 | 1 | 1 | 1 | 1 | 1 |   |   |
| 30 | 400 | 1 | 1 | 1 | 1 | 1 | 1 | 1 |   | 1 |
| 31 | 400 |   | 1 | 1 | 1 |   | 1 |   |   |   |
| 32 | 400 | 1 | 1 | 1 | 1 | 1 | 1 | 4 | 1 | 2 |
|    | 100 |   |   |   |   |   |   |   | 1 | 1 |
|    | 25  |   |   |   |   |   |   |   | 1 | 1 |
| 33 | 400 | 1 | 1 | 1 | 1 | 1 | 1 | 1 | 1 | 4 |
|    | 100 |   |   |   |   |   |   |   |   | 1 |
|    | 25  |   |   |   |   |   |   |   |   | 1 |
| 34 | 400 | 1 | 1 | 1 | 1 | 1 | 1 | 1 | 1 | 1 |

Many of the compounds have been retested in replicated special tests against downy mildew and botrytis rot of grape. The test methods were the same as those described above, except that multiple replicates were used at the various rates. In many cases, the tests reported below have been repeated several times, and the results thereof have been averaged.

| Compound of Example No. | Appln. Rate ppm. | Downy Mildew | Botrytis |
|---|---|---|---|
| 1 | 800 | 5 | 1 |
|   | 400 | 5 | 2 |
|   | 200 | 5 | 1 |
|   | 100 | 4 |   |
|   | 50  | 4 |   |
|   | 25  | 3 |   |
|   | 12.5 | 2 |   |
| 2 | 800 | 5 | 4 |
|   | 400 | 4 | 3 |
|   | 200 | 4 | 1 |
|   | 100 | 1 |   |

| Compound of Example No. | Appln. Rate ppm. | Downy Mildew | Botrytis |
|---|---|---|---|
| 3 | 800 | | 1 |
| | 400 | 5 | 1 |
| | 200 | 4 | 1 |
| | 100 | 4 | |
| | 50 | 4 | |
| | 25 | 3 | |
| 4 | 400 | | 1 |
| | 200 | 1 | 2 |
| | 100 | 1 | 2 |
| | 50 | 2 | 1 |
| 5 | 800 | 5 | 2 |
| | 400 | 5 | 1 |
| | 200 | 5 | 1 |
| | 100 | 1 | |
| 6 | 400 | 5 | 2 |
| | 200 | 5 | 2 |
| | 100 | 4 | 1 |
| | 50 | 4 | 1 |
| 7 | 800 | 5 | 1 |
| | 400 | 5 | 1 |
| | 200 | 4 | 1 |
| | 100 | 1 | |
| | 50 | 1 | |
| 8 | 400 | 5 | |
| | 200 | 1 | |
| | 100 | 2 | |
| | 50 | 2 | |
| 9 | 400 | 5 | |
| | 200 | 2 | |
| | 100 | 1 | |
| | 50 | 1 | |
| 10 | 800 | | 1 |
| | 400 | 4 | 1 |
| | 200 | 2 | 1 |
| | 100 | 3 | 1 |
| | 50 | 2 | 1 |
| 11 | 800 | | 1 |
| | 400 | 5 | 1 |
| | 200 | 5 | 1 |
| | 100 | 4 | 1 |
| | 50 | 4 | 1 |
| | 25 | 5 | |
| 12 | 800 | 5 | 3 |
| | 400 | 5 | 1 |
| | 200 | 4 | 1 |
| | 100 | 4 | |
| | 50 | 4 | |
| | 25 | 1 | |
| 13 | 800 | 5 | 2 |
| | 400 | 5 | 2 |
| | 200 | 5 | 2 |
| | 100 | 4 | |
| | 50 | 3 | |
| | 25 | 3 | |
| 14 | 800 | 5 | 1 |
| | 400 | 5 | 1 |
| | 200 | 5 | 1 |
| | 100 | 3 | |
| | 50 | 3 | |
| 15 | 800 | 5 | 3 |
| | 400 | 5 | 4 |
| | 200 | 5 | 1 |
| | 100 | 5 | |
| | 50 | 4 | |
| | 25 | 2 | |
| 19 | 800 | | 1 |
| | 400 | 5 | 1 |
| | 200 | 5 | 1 |
| | 100 | 5 | |
| | 50 | 3 | |
| | 25 | 4 | |
| | 12.5 | 1 | |
| 20 | 800 | 5 | |
| | 400 | 4 | |
| | 200 | 4 | |
| | 100 | 4 | |
| | 50 | 4 | |
| | 25 | 1 | |
| 21 | 800 | 5 | |
| | 400 | 4 | |
| | 200 | 4 | |
| | 100 | 4 | |
| | 50 | 1 | |
| | 25 | 1 | |
| 26 | 800 | 4 | 1 |
| | 400 | 3 | 1 |
| | 200 | 2 | 1 |
| 27 | 800 | 4 | 1 |
| | 400 | 4 | 1 |
| | 200 | 3 | 1 |
| | 100 | 2 | |
| | 50 | 3 | |
| | 25 | 1 | |
| 28 | 800 | 4 | 1 |
| | 400 | 3 | 1 |
| | 200 | 4 | 1 |
| 29 | 800 | 5 | 1 |
| | 400 | 5 | 1 |
| | 200 | 3 | 1 |
| 30 | 800 | 3 | 1 |
| | 400 | 4 | 1 |
| | 200 | 2 | 1 |
| 31 | 400 | 5 | |
| | 200 | 3 | |
| | 100 | 1 | |
| | 50 | 2 | |
| 32 | 800 | 4 | 1 |
| | 400 | 2 | 1 |
| | 200 | 2 | 1 |
| 33 | 800 | 5 | 1 |
| | 400 | 5 | 1 |
| | 200 | 4 | 1 |
| | 100 | 2 | |
| | 50 | 2 | |
| | 25 | 2 | |
| 34 | 800 | 4 | 1 |
| | 400 | 4 | 2 |
| | 200 | 3 | 1 |

The compound of Example 1 was tested against a heavy infestation of downy mildew of grapes growing in field plots. The compound was applied as 600 and 1200 ppm. aqueous suspensions of a wettable powder formulation. Applications were made on a 7-10 day spray schedule throughout the downy mildew season. When the grapes were under extremely heavy disease pressure, with 82 percent disease involvement in untreated control plots, the 600 ppm. treatment gave 46 percent control, and the 1200 ppm. treatment gave 87 percent control.

While the efficacy of the compounds against fungal foliar phytopathogens is their most important property, they have other significant utilities as well. For example, they control a number of other harmful pathogens, as well as those affecting plants. The following results were obtained when representative compounds were tested in a system to determine their ability to inhibit the growth of microorganisms in vitro. The organisms named below were grown in culture media, appropriate for the growth of the various organisms, containing the compounds at various concentrations, in mcg./ml. The table below lists the lowest concentration at which each compound inhibited the growth of the microorganism.

A. *Staphylococcus aureus* 3055
B. *Staphylococcus aureus* 3074
C. *Klebsiella pneumoniae* KL14
D. *Streptococcus faecalis* X66
E. *Proteus morganii* PR15
F. *Salmonella typhosa* SA12

G. *Bordetella bronchiseptica* 16
H. *Escherichia coli* EC14
I. *Pasteurella multocida* (bovine)
J. *Pasteurella multocida* (avian)
K. *Mycoplasma gallisepticum* 38502
L. *Mycoplasma synoviae*
M. *Mycoplasma hyorhinis*
N. *Mycoplasma hyopneumoniae*
O. *Pseudomonas sp.*
P. *Aeromonas liquefaciens*
Q. *Erwinia amylovora*
R. *Candida tropicalis* A17
S. *Trichophyton mentagrophytes*
T. *Asperigillus flavus*
U. *Ceratocystis ulmi* its reproduction rate and its vigor are decreased, with the result that the express signs of the disease, and the concomitant injury to the host plant, are decreased as compared with phytopathogens growing on untreated plants.

As is usual in the plant protection art, best results are obtained by applying the compound several times during the growing season at intervals of from one to a few weeks, depending on the weather and the severity of the disease.

The methods of formulating the compounds and preparing dispersions of the formulations, and the methods of applying dispersions of the compounds to the plants to be protected, are entirely conventional in the plant protection art. Some explanation of the methods of

| Compound of Example No. | Organism | | | | | | | | | | | | | | | | | | | | |
|---|---|---|---|---|---|---|---|---|---|---|---|---|---|---|---|---|---|---|---|---|---|
| | A | B | C | D | E | F | G | H | I | J | K | L | M | N | O | P | Q | R | S | T | U |
| 2 | <10 | <10 | | 100 | 100 | 100 | | | | | | | | | | | 100 | <10 | <10 | 100 | <10 |
| 3 | <10 | <10 | 100 | 100 | 100 | 100 | | 6 | | 12 | 25 | 50 | 25 | 50 | 50 | 50 | <10 | <10 | <10 | <10 | <10 |
| 5 | <10 | <10 | | | | | | | | | | | | | | | 100 | <10 | <10 | 100 | <10 |
| 6 | <10 | 100 | | | | | | | | | | | | | | | | | | | |
| 8 | <10 | <10 | | 100 | 100 | 100 | <10 | | | | | | | | | | <10 | <10 | <10 | <10 | <10 |
| 9 | <10 | 100 | | 100 | | | 100 | | | | | | | | | | 100 | <10 | <10 | 100 | <10 |
| 10 | 100 | 100 | | | | | | | | | | | | | | | 100 | 100 | <10 | 100 | <10 |
| 11 | <10 | 100 | | | | | | | | | | | | | | | | 100 | 100 | | 100 |
| 12 | <10 | <10 | | 100 | | | | | | | | | | | | | 100 | <10 | <10 | <10 | <10 |
| 13 | <10 | <10 | | | | | <10 | | | | | | | | | | | <10 | .2 | <10 | |
| 14 | <10 | <10 | | 100 | | | <10 | | | | | | | | | | | <10 | .02 | <10 | <10 |
| 16 | <10 | | | | | | | | | | | | | | | | | 100 | 100 | | 100 |
| 17 | <10 | 100 | | 100 | 100 | 100 | 100 | 100 | | | | | | | | | <10 | 100 | <10 | 100 | <10 |
| 18 | <10 | <10 | | | | | 100 | | | | | | | | | | | <10 | <10 | | <10 |
| 19 | <10 | <10 | | | | | <10 | | | | | | | | | | | <10 | <10 | 100 | <10 |
| 20 | 100 | 100 | | 100 | | | | | | | | | | | | | 100 | | 100 | 100 | 100 |
| 21 | | | | | | | | | | | | | | | | | | | 100 | | |
| 32 | | | 100 | | | | | | | | | | | | | | | | | | |

Many of the compounds have also been found to be effective against aquatic weeds. For example, the compounds of Examples 2, 3, 5, 7, 8, 9, 12, 13, 14, 16, 17, 18, 19 and 20 have been found to be effective against coontail, *Ceratophyllum demersum* L., hydrilla, *Hydrilla verticillata*, and duckweed, *Lemna minor* L., at concentrations of 10 ppm. or less. Further, the compound of Example 9 has been found to be active against the above weeds, and also against naiad, *Najas marina* L., and cabomba, *Cabomba caroliniana*, at concentrations as low as 2 ppm.

The test data reported above show that the compounds of this invention are useful for the protection of plants from the adverse effects of a variety of fungal foliar phytopathogens. Accordingly, an important aspect of the invention is a new method of reducing the adverse effects of fungal foliar phytopathogens which comprises contacting the phytopathogens on the foliage of host plants with an effective phytopathogen-inhibiting amount of one of the compounds described above. The method is carried out by applying a compound of the invention to the plants to be protected.

Practice of the method does not necessarily kill the phytopathogens. As the data above show, application of a phytopathogen-inhibiting amount of a compound reduces the adverse effects of the disease, even though only a part of the phytopathogen population may be killed by the compound. The term "phytopathogen-inhibiting amount" is used here to describe an amount which is sufficient to reduce the adverse effects of a phytopathogen. The term "reducing the adverse effects" refers to weakening the pathogen sufficiently that application will be given merely to assure that those skilled in the art can carry out the invention without undue experimentation.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plants being treated, and the quantity of plant protecting compound is dependent upon its concentration in the dispersion. In general, compound concentrations in the range of from about 50 to about 1500 parts of compound per million parts by weight dispersion are used in the practice of this invention.

The compounds of this invention are usually applied in the form of fungicidal compositions which are important embodiments of the invention. Such compositions comprise a compound of this invention and a phytologically-acceptable inert carrier, and are either concentrated formulations which are dispersed in water for application, or are dust formulations. The compositions are prepared according to procedures and formulae which are conventional in the agricultural chemical art, but which are novel and important because of the presence therein of the compounds of this invention. Some description of the formulation of the fungicidal compositions will be given, to assure that agricultural chemists can readily prepare any desired fungicidal composition.

The dispersions in which the compounds are applied are most often aqueous suspensions or emulsions prepared from concentrated compositions of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as terpenic solvents including rosen derivatives, and complex alcohols such as 2-ethoxyethanol. Suitable emulsifiers for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied to foliage in the form of dusts. Agricultural chemical dusts typically comprise the compound in a finely powdered form, dispersed in a powdered inert carrier. Most often, the carrier is a powdered clay, such as pyrophyllite, bentonite, a volcanic deposit, or montmorillonite. Dusts are usually prepared to contain concentrations of the compound at the highest part of the concentration range, such as 1500 ppm., and may contain even more active ingredient.

Dispersions of the compounds are applied in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

I claim:

1. A compound of the formula

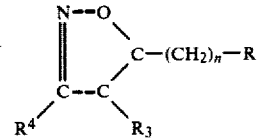

wherein
R represents NCS;
n represents 1 or 2;
R$^3$ represents hydrogen or phenyl;
R$^4$ represents 2-pyridyl.

2. A compound of claim 1 wherein R$^3$ represents hydrogen.

3. The compound of claim 2 which is 5-isothiocyanatomethyl-3-(2-pyridyl)-2-isoxazoline.

4. A fungicidal composition comprising a fungicidally effective amount of a compound of claim 1 and a phytologically-acceptable inert carrier.

5. A fungicidal composition comprising a fungicidally effective amount of a compound of claim 2 and a phytologically-acceptable inert carrier.

6. The composition of claim 5 wherein the compound is 5-isothiocyanatomethyl-3-(2-pyridyl)-2-isoxazoline.

7. The method of reducing the adverse effects of fungal foliar phytopathogens which comprises contacting the phytopathogens on the foliage of host plants with an effective phytopathogen-inhibiting amount of a compound of claim 1.

8. A method of reducing the adverse effects of fungal foliar phytopathogens which comprises contacting the phytopathogens on the foliage of host plants with an effective phytopathogen-inhibiting amount of a compound of claim 2.

9. The method of claim 8 wherein the compound is 5-isothiocyanatomethyl-3-(2-pyridyl)-2-isoxazoline.

* * * * *